United States Patent
Cates et al.

(10) Patent No.: US 7,499,758 B2
(45) Date of Patent: Mar. 3, 2009

(54) HELICAL FIXATION ELEMENTS FOR SUBCUTANEOUS ELECTRODES

(75) Inventors: Adam W. Cates, Minneapolis, MN (US); Ron Heil, Roseville, MN (US); Pete Kelley, Buffalo, MN (US); Curtis Charles Lindstrom, Roseville, MN (US); Jason Alan Shiroff, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 158 days.

(21) Appl. No.: 10/739,918

(22) Filed: Dec. 18, 2003

(65) Prior Publication Data

US 2004/0230280 A1 Nov. 18, 2004

Related U.S. Application Data

(60) Provisional application No. 60/462,272, filed on Apr. 11, 2003.

(51) Int. Cl.
*A61N 1/00* (2006.01)
(52) U.S. Cl. .................................................. 607/126
(58) Field of Classification Search .............. 607/8, 607/5, 119, 4, 115, 116, 122, 126–128, 131, 607/118, 134
See application file for complete search history.

(56) References Cited

U.S. PATENT DOCUMENTS

| | | | |
|---|---|---|---|
| 3,902,501 A | 9/1975 | Citron et al. | |
| 4,301,815 A | 11/1981 | Doring | |
| 4,519,404 A | 5/1985 | Fleischhacker | |
| 4,542,752 A | 9/1985 | DeHaan et al. | |
| 4,562,841 A | 1/1986 | Brockway et al. | |
| 4,716,888 A | 1/1988 | Wesner | |
| 4,819,661 A | 4/1989 | Heil, Jr. et al. | |
| 4,819,662 A | 4/1989 | Heil, Jr. et al. | |

(Continued)

FOREIGN PATENT DOCUMENTS

EP 0 517 494 A 12/1992

(Continued)

OTHER PUBLICATIONS

Renee Hartz et al., *New Approach to Defibrillator Insertion*, J. Thoracic Cardiovascular Surgery, vol. 97, pp. 920-922 (1989).

(Continued)

*Primary Examiner*—George Manuel
(74) *Attorney, Agent, or Firm*—Hollingsworth & Funk, LLC

(57) ABSTRACT

Subcutaneous leads that incorporate active fixation elements including, for example, helical coils, provide for fixation of cardiac lead components within a patient. An implantable lead includes a lead body with a supported electrode configured for subcutaneous non-intrathoracic placement within a patient. A fixation element is provided on the implantable lead and configured to actively secure one or both of the subcutaneous electrode and the lead body in tissue. A delivery apparatus comprising a sheath may be employed that is configured to introduce the lead to a desired subcutaneous non-intrathoracic location. Lead delivery typically involves introducing a sheath into a subcutaneous non-intrathoracic body location of a patient, providing a lead supporting an electrode, advancing the lead through the sheath, actively fixing the lead to tissue, and thereafter removing the sheath from the patient.

25 Claims, 18 Drawing Sheets

U.S. PATENT DOCUMENTS

| | | |
|---|---|---|
| 4,827,940 A | 5/1989 | Mayer et al. |
| 4,913,164 A | 4/1990 | Greene et al. |
| 4,953,551 A | 9/1990 | Mehra et al. |
| 5,005,587 A | 4/1991 | Scott |
| 5,036,849 A | 8/1991 | Hauck et al. |
| 5,113,869 A | 5/1992 | Nappholz et al. |
| 5,133,353 A | 7/1992 | Hauser |
| 5,170,784 A | 12/1992 | Ramon et al. |
| 5,179,945 A | 1/1993 | Van Hofwegen et al. |
| 5,203,348 A | 4/1993 | Dahl et al. |
| 5,209,229 A | 5/1993 | Gilli |
| 5,230,337 A | 7/1993 | Dahl et al. |
| 5,261,400 A | 11/1993 | Bardy |
| 5,284,136 A | 2/1994 | Hauck et al. |
| 5,292,338 A | 3/1994 | Bardy |
| 5,300,106 A * | 4/1994 | Dahl et al. ................ 607/119 |
| 5,301,677 A | 4/1994 | Hsung |
| 5,313,953 A | 5/1994 | Yomtov et al. |
| 5,314,430 A | 5/1994 | Bardy |
| 5,314,459 A | 5/1994 | Swanson et al. |
| 5,331,966 A | 7/1994 | Bennett et al. |
| 5,360,442 A | 11/1994 | Dahl et al. |
| 5,366,493 A | 11/1994 | Scheiner et al. |
| 5,366,496 A | 11/1994 | Dahl et al. |
| 5,372,606 A | 12/1994 | Lang et al. |
| 5,376,106 A | 12/1994 | Stahmann et al. |
| 5,378,239 A | 1/1995 | Termin et al. |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,411,539 A | 5/1995 | Neisz |
| 5,411,546 A * | 5/1995 | Bowald et al. ............. 607/126 |
| 5,439,482 A | 8/1995 | Adams et al. |
| 5,441,518 A | 8/1995 | Adams et al. |
| 5,468,254 A | 11/1995 | Hahn et al. |
| 5,507,751 A | 4/1996 | Goode et al. |
| 5,522,876 A * | 6/1996 | Rusink ....................... 607/127 |
| 5,531,779 A | 7/1996 | Dahl et al. |
| 5,545,202 A | 8/1996 | Dahl et al. |
| 5,545,207 A | 8/1996 | Smits et al. |
| 5,603,732 A | 2/1997 | Dahl et al. |
| 5,620,466 A | 4/1997 | Haefner et al. |
| 5,632,749 A * | 5/1997 | Goode et al. ............... 606/108 |
| 5,634,938 A | 6/1997 | Swanson et al. |
| 5,641,326 A | 6/1997 | Adams |
| 5,662,688 A | 9/1997 | Haefner et al. |
| 5,683,447 A | 11/1997 | Bush et al. |
| 5,697,953 A | 12/1997 | Kroll et al. |
| 5,704,365 A | 1/1998 | Albrecht et al. |
| 5,724,984 A | 3/1998 | Arnold et al. |
| 5,728,140 A | 3/1998 | Salo et al. |
| 5,827,326 A | 10/1998 | Kroll et al. |
| 5,895,414 A | 4/1999 | Sanchez-Zambrano |
| 5,902,329 A | 5/1999 | Hoffmann et al. |
| 5,916,243 A | 6/1999 | KenKnight et al. |
| 5,951,597 A | 9/1999 | Tockman et al. |
| 5,957,956 A | 9/1999 | Kroll et al. |
| 5,964,795 A * | 10/1999 | McVenes et al. ............ 607/122 |
| 6,044,298 A | 3/2000 | Salo et al. |
| 6,055,454 A | 4/2000 | Heemels |
| 6,078,840 A | 6/2000 | Stokes |
| 6,136,021 A | 10/2000 | Chastain et al. |
| 6,148,230 A | 11/2000 | KenKnight |
| 6,227,072 B1 | 5/2001 | Ritchey et al. |
| 6,259,953 B1 * | 7/2001 | Lucchesi et al. ............ 607/119 |
| 6,270,457 B1 | 8/2001 | Bardy |
| 6,280,380 B1 | 8/2001 | Bardy |
| 6,280,462 B1 | 8/2001 | Hauser et al. |
| 6,304,786 B1 | 10/2001 | Heil et al. |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,398,728 B1 | 6/2002 | Bardy |
| 6,409,675 B1 | 6/2002 | Turcott |
| 6,415,174 B1 | 7/2002 | Bebehani et al. |
| 6,438,410 B2 | 8/2002 | Hsu et al. |
| 6,440,066 B1 | 8/2002 | Bardy |
| 6,480,733 B1 | 11/2002 | Turcott |
| 6,491,639 B1 | 12/2002 | Turcott |
| 6,512,940 B1 | 1/2003 | Brabec et al. |
| 6,512,957 B1 | 1/2003 | Witte |
| 6,522,915 B1 | 2/2003 | Ceballos et al. |
| 6,564,106 B2 | 5/2003 | Guck et al. |
| 6,567,704 B2 * | 5/2003 | Sundquist et al. ........... 607/119 |
| 6,592,581 B2 | 7/2003 | Bowe |
| 6,607,509 B2 | 8/2003 | Bobroff et al. |
| 6,615,083 B2 | 9/2003 | Kupper |
| 6,622,046 B2 | 9/2003 | Fraley et al. |
| 6,697,677 B2 | 2/2004 | Dahl et al. |
| 6,721,597 B1 * | 4/2004 | Bardy et al. ................... 607/4 |
| 2002/0016622 A1 | 2/2002 | Heil et al. |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035379 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082658 A1 | 6/2002 | Heinrich et al. |
| 2002/0091414 A1 | 7/2002 | Bardy et al. |
| 2002/0095184 A1 | 7/2002 | Bardy et al. |
| 2002/0103510 A1 | 8/2002 | Bardy et al. |
| 2002/0107544 A1 | 8/2002 | Ostroff et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0111663 A1 | 8/2002 | Dahl et al. |
| 2002/0120299 A1 | 8/2002 | Ostroff et al. |
| 2002/0161423 A1 | 10/2002 | Lokhoff et al. |
| 2003/0004546 A1 | 1/2003 | Casey |
| 2003/0004552 A1 | 1/2003 | Plombon et al. |
| 2003/0023175 A1 | 1/2003 | Arzbaecher et al. |
| 2003/0036778 A1 | 2/2003 | Ostroff et al. |
| 2003/0045904 A1 | 3/2003 | Bardy et al. |
| 2003/0069609 A1 | 4/2003 | Thompson |
| 2003/0088278 A1 | 5/2003 | Bardy et al. |
| 2003/0088279 A1 | 5/2003 | Rissmann et al. |
| 2003/0088280 A1 | 5/2003 | Ostroff |
| 2003/0088281 A1 | 5/2003 | Ostroff et al. |
| 2003/0088282 A1 | 5/2003 | Ostroff |
| 2003/0088283 A1 | 5/2003 | Ostroff |
| 2003/0088286 A1 | 5/2003 | Ostroff et al. |
| 2003/0097153 A1 | 5/2003 | Bardy et al. |
| 2003/0212436 A1 | 11/2003 | Brown |
| 2004/0064176 A1* | 4/2004 | Min et al. ................... 607/126 |

FOREIGN PATENT DOCUMENTS

| | | |
|---|---|---|
| EP | 0 941 695 A | 9/1999 |
| WO | WO 92/20402 | 11/1992 |

| | | |
|---|---|---|
| WO | WO 96/04955 A | 2/1996 |

OTHER PUBLICATIONS

John C. Schuder et al., *Transthoracic Ventricular Defibrillation in the Dog with Truncated and Untruncated Exponential Stimuli*, IEEE Trans. On Bio-Medical Engin., vol. BME-18, No. 6, pp. 410-415 (Nov. 1971).

John C. Schuder et al., *Ventricular Defibrillation in the Dog Using Implanted and Partially Implanted Electrode Systems*, Am. J. of Cardiology, vol. 33, pp. 243-247 (Feb. 1974).

John C. Schuder et al., *Experimental Ventricular Defibrillation with an Automatic and Completely Implanted System*, Trans. Am. Soc. Artif. Int. Organs, vol. 16, pp. 207-212 (1970).

Karel Smits & Marek Malik, *Defibrillation Threshold (DFT) Model of a Fully Subcutaneous ICD System*, Europace Supplements, vol. 2, Jun. 2001 at col. 778, p. B83.

Stirbis et al., *Optmizing the Shape of Implanted Artificial Pacemakers*, Kaunas Medical Institute. Translated from Meditsinskaya Tekhnika, No. 6, pp. 25-27 (1985).

Charles T. Leng et al., *Lead Configuration for Defibrillator Implantation in a Patient with Congenital Heart Disease and a Mechanical Prosthetic Tricuspid Valve*, PACE, vol. 24, No. 8, pp. 1291-1292 (Aug. 2001).

Park & Pollock, *Use of an Implantable Cardioverter Defibrillator in an Eight-Month-Old Infant with Ventricular Fibrillation Arising from a Myocardial Fibroma*, PACE, vol. 22, No. 1, pp. 138-139 (Jan. 1999).

Rainer Gradaus M.D. et al., *Nonthoracotomy Implantable Cardioverter Defibrillator Placement in Children: Use of a Subcutaneous Array Leads and Abdominally Placed Implantable Cardioverter Defibrillators in Children*, J. of Cardiovascular Electrophysiology, vol. 12, No. 3, pp. 356-360 (Mar. 2001).

* cited by examiner

HELICAL FIXATION ELEMENTS FOR SUBCUTANEOUS ELECTRODES

RELATED APPLICATIONS

This application claims the benefit of Provisional Patent Application Ser. No. 60/462,272, filed on Apr. 11, 2003, to which priority is claimed pursuant to 35 U.S.C. §119(e) and which is hereby incorporated herein by reference.

FIELD OF THE INVENTION

The present invention relates generally to leads for subcutaneously implantable cardiac monitoring and/or stimulation devices, and, more particularly, to helical fixation elements for subcutaneous electrodes.

BACKGROUND OF THE INVENTION

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for monitoring the heart's electrical signals and for delivering pulses to the heart in accordance with various therapies for treating arrhythmias.

Typical implantable cardioverter/defibrillators (ICDS) include one or more endocardial leads to which at least one defibrillation electrode is connected. Such ICDs are capable of delivering high-energy shocks to the heart, interrupting the ventricular tachyarrythmia or ventricular fibrillation, and allowing the heart to resume normal sinus rhythm. ICDs may also include pacing functionality.

Although ICDs are very effective at preventing Sudden Cardiac Death (SCD), most people at risk of SCD are not provided with implantable defibrillators. Primary reasons for this unfortunate reality include the limited number of physicians qualified to perform transvenous lead/electrode implantation, a limited number of surgical facilities adequately equipped to accommodate such cardiac procedures, and a limited number of the at-risk patient population that may safely undergo the required endocardial or epicardial lead/electrode implant procedure. For these reasons, subcutaneous ICDs are being developed.

Current ICDs utilize subcutaneous electrodes that may be prone to migrate in the subcutaneous tissue layer due to, for example, gravity, patient mobility, or patient interaction (e.g., twiddler's syndrome). Such migration may be detrimental to the performance of a subcutaneous electrode system because monitoring, detection, and defibrillation efficacy is typically very sensitive to electrode position/orientation.

Existing subcutaneous leads have typically relied on redundancy to address the problem of subcutaneous electrode migration. For example, a subcutaneous array may include three long coil electrodes, even though all three coils are not necessary when properly placed. Because migration may occur, the three long fingers provide adequate coverage to maintain defibrillation efficacy.

There is a need for more precise electrode placement that solves the problem of subcutaneous electrode migration. There is a further need for a fixation approach for subcutaneous leads that provides for improved subcutaneous system performance, such as by providing more consistent defibrillation and/or pacing thresholds and potentially lowering such thresholds. The present invention fulfills these and other needs, and addresses deficiencies in known systems and techniques.

SUMMARY OF THE INVENTION

The present invention is directed to subcutaneous leads that, in general, may be fixed in tissue after placement of the lead at an implant site. Embodiments of the present invention are directed to subcutaneous leads that incorporate fixation elements including, for example, helical coils. Further embodiments of the present invention are directed to methods of placement and methods of fixation of subcutaneously implantable leads.

One embodiment in accordance with the present invention is directed to an implantable lead including a lead body with a supported subcutaneous electrode. The subcutaneous electrode is configured for subcutaneous non-intrathoracic placement within a patient. A fixation element is provided on the implantable lead and configured to secure one or both of the subcutaneous electrode and the lead body in subcutaneous non-intrathoracic tissue.

Another embodiment of a lead in accordance with the present invention is directed to an implantable lead system that includes a lead body having a body cross-sectional diameter. A subcutaneous electrode is supported by the lead body, the subcutaneous electrode configured for subcutaneous non-intrathoracic placement within a patient. A fixation element is provided on the implantable lead, the fixation element configured to secure the lead in subcutaneous non-intrathoracic tissue. A delivery apparatus comprising a sheath may be included that is configured to introduce the lead to a desired subcutaneous non-intrathoracic location within the patient.

The lead may have a fixation element with a cross-sectional diameter larger than the lead body's cross-sectional diameter. In another embodiment, the lead has a lead longitudinal axis and the fixation element has a fixation element longitudinal axis, and the lead longitudinal axis is non-coincident with respect to the fixation element longitudinal axis.

A method of lead delivery in accordance with an embodiment of the present invention involves introducing a sheath into a subcutaneous non-intrathoracic body location of a patient, providing a lead comprising a lead body and a subcutaneous electrode, and advancing the lead through the sheath and to the subcutaneous non-intrathoracic body location. The method further involves fixing the lead to subcutaneous non-intrathoracic tissue and thereafter removing the sheath from the patient. The method may also involve longitudinally splitting the sheath when retracting the sheath from the patient and enabling a fixation element for active engagement with subcutaneous non-intrathoracic tissue.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
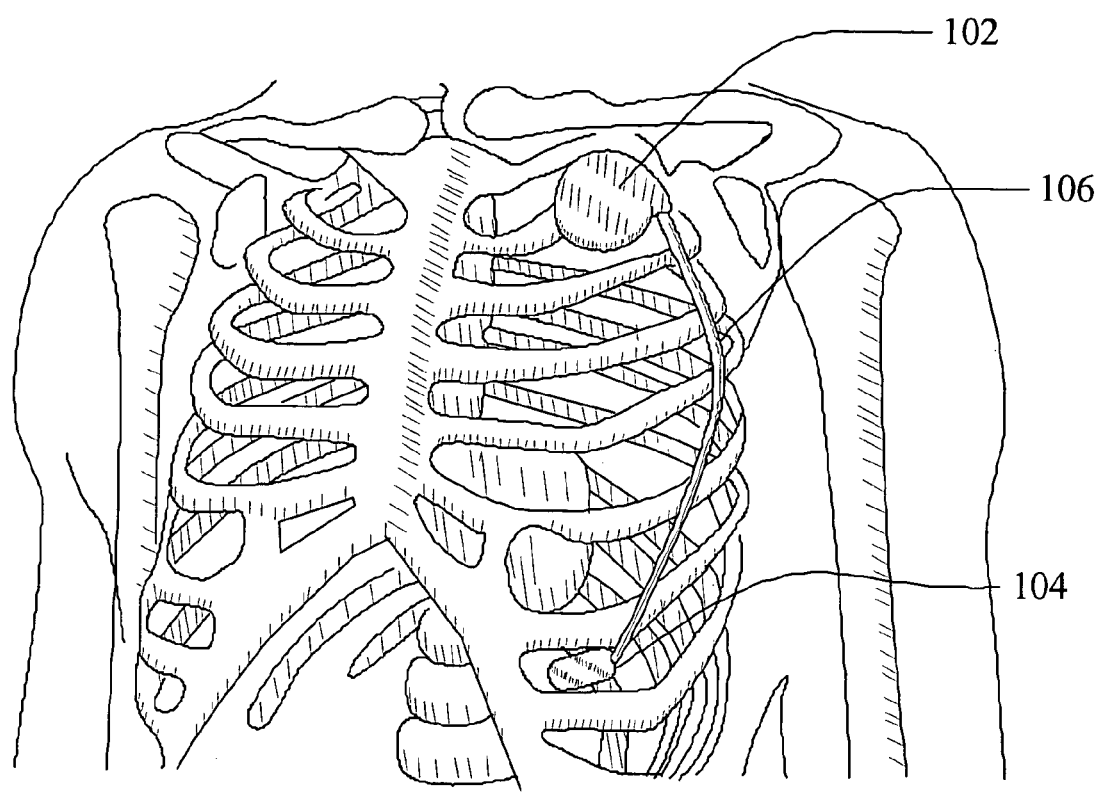
FIGS. 1A and 1B are views of a transthoracic cardiac monitoring and/or stimulation device as implanted in a patient.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration various embodiments in which the invention may be practiced. It is to be understood that other embodiments may be utilized, and structural and functional changes may be made without departing from the scope of the present invention.

A device employing an implantable lead implemented in accordance with the present invention may incorporate one or more of the features, structures, methods, or combinations thereof described herein below. For example, a subcutaneous cardiac monitor or stimulator may be implemented to include one or more of the features and/or processes described below. It is intended that such a device or method need not include all of the features and functions described herein, but may be implemented to include selected features and functions that, in combination, provide for unique structures and/or functionality.

In general terms, an implantable lead implemented in accordance with the present invention may be used with a subcutaneous cardiac monitoring and/or stimulation device. One such device is an implantable transthoracic cardiac monitoring and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for monitoring cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more leads incorporating electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

Figure 1B:
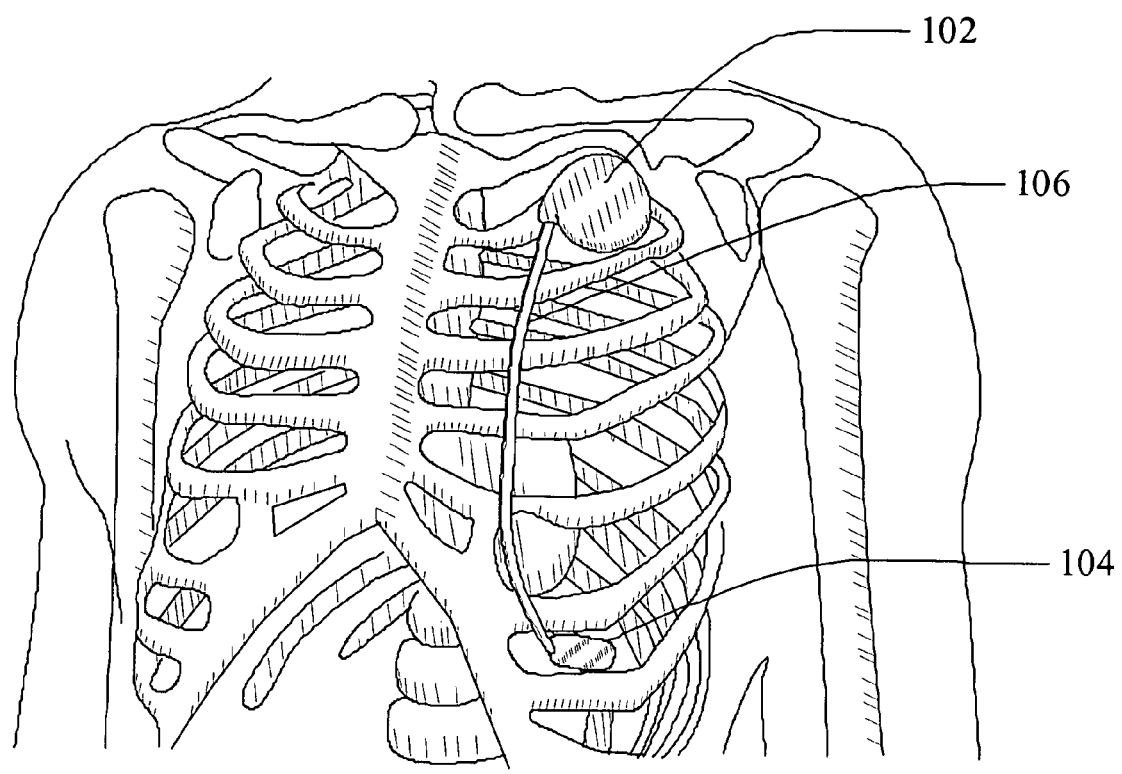

Referring now to FIGS. 1A and 1B of the drawings, there is shown a configuration of an ITCS device implanted in the chest region of a patient at different locations by use of a dissection tool. In the particular configuration shown in FIGS. 1A and 1B, the ITCS device includes a housing 102 within which various cardiac monitoring, detection, processing, and energy delivery circuitry may be housed. The housing 102 is typically configured to include one or more electrodes (e.g., can electrode and/or indifferent electrode). Although the housing 102 is typically configured as an active can, it is appreciated that a non-active can configuration may be implemented, in which case at least two electrodes spaced apart from the housing 102 are employed. An ITCS system according to this approach is distinct from conventional approaches in that it is preferably configured to include a combination of two or more electrode subsystems that are implanted subcutaneously.

In the configuration shown in FIGS. 1A and 1B, a subcutaneous electrode 104 may be positioned under the skin in the chest region and situated distal from the housing 102. The subcutaneous and, if applicable, housing electrode(s) may be positioned about the heart at various locations and orientations, such as at various anterior and/or posterior locations relative to the heart. The subcutaneous electrode 104 is electrically coupled to circuitry within the housing 102 via a lead assembly 106. One or more conductors (e.g., coils or cables) are provided within the lead assembly 106 and electrically couple the subcutaneous electrode 104 with circuitry in the housing 102. One or more sense, sense/pace or defibrillation electrodes may be situated on the elongated structure of the electrode support, the housing 102, and/or the distal electrode assembly (shown as subcutaneous electrode 104 in the configuration shown in FIGS. 1A and 1B).

In one configuration, the lead assembly 106 is generally flexible. In another configuration, the lead assembly 106 is constructed to be somewhat flexible, yet has an elastic, spring, or mechanical memory that retains a desired configuration after being shaped or manipulated by a clinician. For example, the lead assembly 106 may incorporate a gooseneck or braid system that may be distorted under manual force to take on a desired shape. In this manner, the lead assembly 106 may be shape-fit to accommodate the unique anatomical configuration of a given patient, and generally retains a customized shape after implantation. Shaping of the lead assembly 106 according to this configuration may occur prior to, and during, ITCS device implantation.

In accordance with a further configuration, the lead assembly 106 includes a rigid electrode support assembly, such as a rigid elongated structure that positionally stabilizes the subcutaneous electrode 104 with respect to the housing 102. In this configuration, the rigidity of the elongated structure maintains a desired spacing between the subcutaneous electrode 104 and the housing 102, and a desired orientation of the subcutaneous electrode 104/housing 102 relative to the patient's heart. The elongated structure may be formed from a structural plastic, composite or metallic material, and includes, or is covered by, a biocompatible material. Appropriate electrical isolation between the housing 102 and the subcutaneous electrode 104 is provided in cases where the elongated structure is formed from an electrically conductive material, such as metal.

In one configuration, the rigid electrode support assembly and the housing 102 define a unitary structure (i.e., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have, for example, an arcuate or angled shape.

According to another configuration, the rigid electrode support assembly defines a physically separable unit relative to the housing 102. The rigid electrode support assembly includes mechanical and electrical couplings that facilitate mating engagement with corresponding mechanical and electrical couplings of the housing 102. For example, a header block arrangement may be configured to include both electrical and mechanical couplings that provide for mechanical and electrical connections between the rigid electrode support assembly and housing 102. The header block arrangement may be provided on the housing 102 or the rigid electrode support assembly or both. Alternatively, a mechanical/electrical coupler may be used to establish mechanical and electrical connections between the rigid electrode support assembly and the housing 102. In such a configuration, a variety of different electrode support assemblies of varying shapes, sizes, and electrode configurations may be made available for physically and electrically connecting to a standard ITCS device.

It is noted that the electrodes and the lead assembly 106 may be configured to assume a variety of shapes. For example, the lead assembly 106 may have a wedge, chevron, flattened oval, or a ribbon shape, and the subcutaneous electrode 104 may include a number of spaced electrodes, such as an array or band of electrodes. Moreover, two or more subcutaneous electrodes 104 may be mounted to multiple electrode support assemblies 106 to achieve a desired spaced relationship amongst the subcutaneous electrodes 104. Accordingly, subcutaneous leads of the present invention may be shaped appropriately for specific electrodes or families of electrodes and electrode support assemblies.

Figure 2:
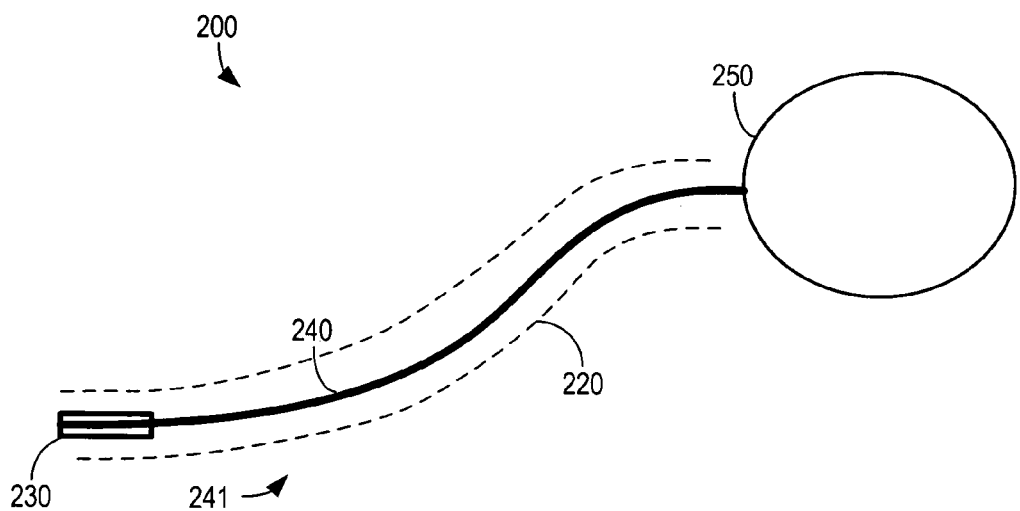
FIG. 2 illustrates a lead in accordance with the present invention, inserted in a dissected subcutaneous path leading from the can.

Referring now to FIG. 2, an ITCS system 200 is illustrated which includes a can 250 with a lead 241 inserted into a subcutaneous dissection path 220. The lead 241 includes an electrode 230 and a lead body 240. The electrode 230 is here illustrated at the distal end of the lead body 240. The subcutaneous dissection path 220 lies within subcutaneous tissue of a patient as illustrated in FIGS. 1A and 1B. The lead 241 may be inserted into the subcutaneous dissection path 220 by itself, or may also be inserted with use of a sheath 320 as illustrated in FIG. 3A.

Figure 3A:
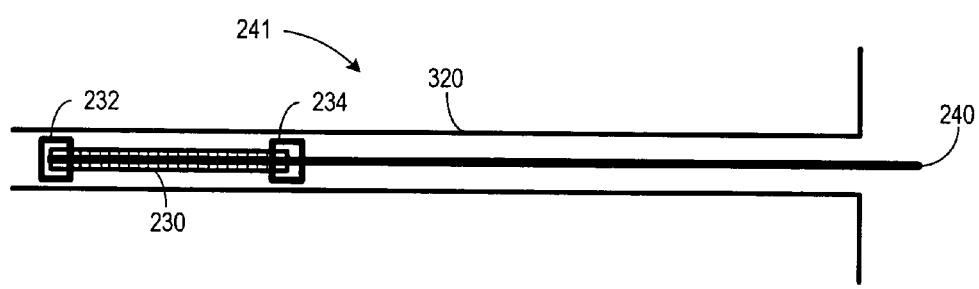
FIG. 3A is a plan view of a lead enclosed within a sheath prior to deployment of fixation elements in accordance with the present invention.

In FIG. 3A, a proximal end of the lead body 240 extends from the sheath 320, with the electrode 230 enclosed within the lumen of the sheath 320. The electrode 230 is illustrated that includes fixation elements 232 and 234 respectively provided at distal and proximal ends of the electrode 230. It should be understood that any number of such fixation elements may be employed to fix the electrode 230 within subcutaneous tissue.

The fixation elements 232 and 234 may include, for example, an expandable fixation mechanism, such as a spongy material that is preferably, but not necessarily, compressed within the lumen of the sheath 320 during delivery. According to one delivery approach, the lead 241 may be inserted into the dissection path, such as dissection path 220 shown in FIG. 2, while inside the sheath 320. After positioning the sheath 320 at the desired location within subcutaneous tissue, the sheath 320 may be retracted or otherwise separated from the lead 241. Retracting the sheath 320 from the electrode 230 and the lead body 240 permits the fixation elements 232 and 234 to expand and affix the electrode 230 within the subcutaneous tissue.

A suitable material for constructing the fixation elements 232 and 234 is Scleral sponge. However, the fixation elements 232 and 234 may be constructed from any implantable material capable of expansion. Expansion of the fixation elements 232 and 234 may occur due to their release from the sheath 320, from uptake of body fluid, from an injected material, or other means of expansion. For example, a fluid may be injected into an expandable balloon fixation element with a one-way valve or stopper.

Figure 3B:
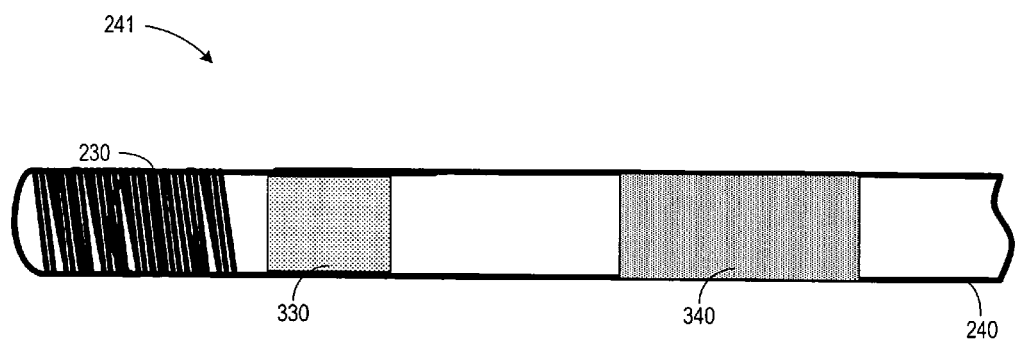
FIGS. 3B and 3C are plan views of a lead having an expanding region before (FIG. 3B) and after (FIG. 3C) expansion in accordance with the present invention.
Figure 3C:
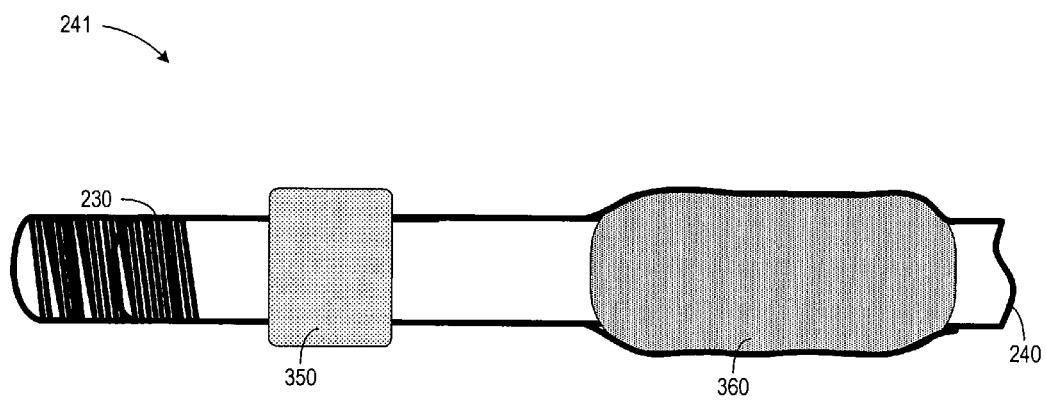

Other embodiments of expanding fixation elements are illustrated in FIGS. 3B and 3C. In FIG. 3B an expanding collar 330 and an expanding lead portion 340 are illustrated in their pre-expansion configuration. The expanding collar 330 and lead portion 340 may, for example, be components made of a mixture of a biocompatible polymer and a water-soluble additive. By way of illustration, silicone rubber and a water-soluble additive such as glycerol represent one combination of materials useful for producing the expanding collar 330 and the expanding lead portion 340.

This combination of materials expands after implantation due to water ingression via osmosis. Utilizing a polymer/additive composition, the absorbed water supplied by the body's aqueous environment penetrates the polymer and dissolves isolated additive particles to provide component expansion. The subsequent reaction forces generated within the polymeric phase eventually balances the osmotic forces so that destructive expansion does not occur. The expanded tip or collar 330 may itself provide a press-fit within the pocket, ensuring fixation. In addition, by using other compositions, the water pockets may combine within the component sufficiently to create pores that communicate with the component surface, which promotes tissue ingrowth.

FIG. 3C illustrates an expanded collar 350 and an expanded lead portion 360. After implantation, collar 330 and lead portion 340 (shown in FIG. 3B) expand, and transform into expanded collar 350 and expanded lead portion 360. The expanded collar 350 and portion 360 may be employed in combination and/or by themselves, to fix the lead 241 into tissue.

Figure 4:
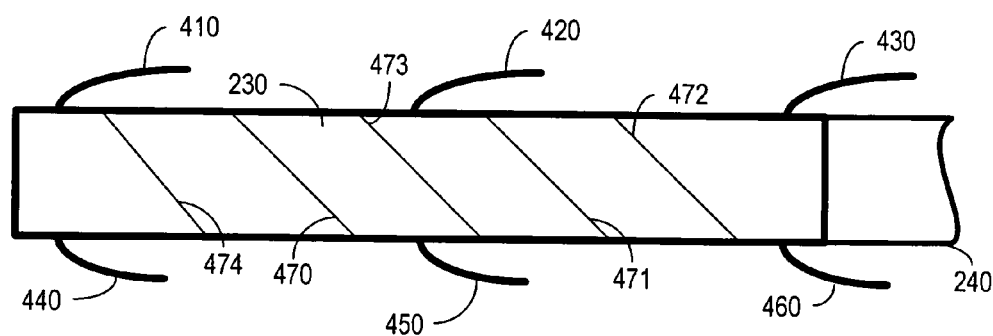
FIG. 4 is a magnified view of one embodiment of a lead having an electrode, the lead implemented to include fixation arrangements in accordance with the present invention.

Turning now to FIG. 4, there is illustrated an embodiment of the lead 241 that includes an electrode 230 provided with another fixation arrangement. The lead 241 is shown to include the electrode 230 now having tines 410, 420, 430, 440, 450, and 460 projecting outwardly from the body of the electrode 230/lead body 240. Also illustrated are a number of diagonal grooves 470, 471, 472, 473, and 474.

The tines 410-460 are shown biased away from the lead body 240 by, for example, manufacturing the tines 410-460 using a mechanically elastic material having spring-like qualities such as, for example, metal or plastic. The tines 410-460 may be angled away and proximally oriented, as illustrated in FIG. 4, to allow the lead 241 to be easily inserted into the dissection path in a distal direction, but resist being pulled out in a proximal direction. The tines 410-460 provide for acute fixation of the lead 241 into subcutaneous tissue.

Figure 5:
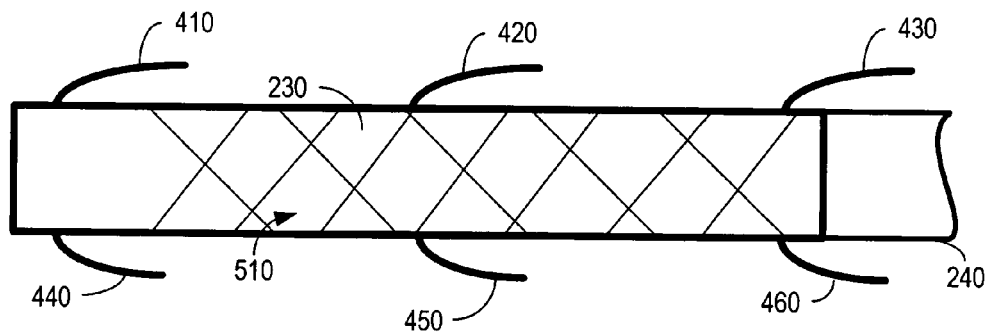
FIG. 5 is a magnified view of another embodiment of a lead having an electrode, the lead implemented to include fixation arrangements in accordance with the present invention.

After placement and acute fixation of the lead 241 within subcutaneous tissue, the grooves 470-474 provide regions for promoting tissue ingrowth, which chronically fixes the lead 241 within the subcutaneous tissue. The grooves 470-474 are denoted by a series of parallel lines oriented diagonally relative to a longitudinal axis of the lead body 240. It is contemplated that any number of grooves may be implemented at any angle or at varying angles. For example, a crosshatched pattern of grooves 510, as is illustrated in FIG. 5, may be incorporated to promote tissue ingrowth after placement of the lead 241 within subcutaneous tissue. The grooves 470-474 may be of any suitable size, shape, depth or spacing.

Figure 6:
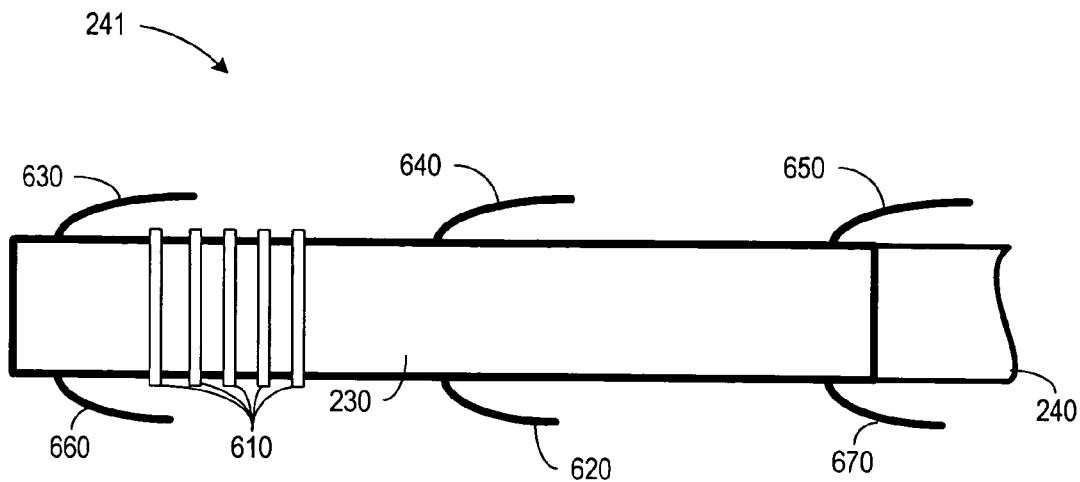
FIG. 6 is a magnified view of a further embodiment of a lead having an electrode, the lead implemented to include fixation arrangements in accordance with the present invention.

As illustrated in FIG. 6, one or more ridges 610 may be used in combination with, or in lieu of, grooves for chronic tissue purchase. The ridges 610 may be configured to provide for chronic fixation of the lead body 240 resulting from tissue ingrowth. Both grooves 510 (FIG. 5) and ridges 610 may also provide a degree of acute fixation, depending on the size of the grooves 510 or ridges 610. Acutely, the grooves 510 or ridges 610 would provide an initial purchase with the tissue. As time progresses, the initial immature encapsulation will constrict, resulting in a more firm purchase on the lead 241. As is further illustrated in FIG. 6, a plurality of tines 620, 630, 640, 650, 660, and 670 may be used in combination with other fixation techniques for purposes of acutely fixing the lead body 240 and/or a lead electrode, as described earlier. Features such as the plurality of tines 620, 630, 640, 650, 660, and 670 may be located on the lead body 240 and/or the electrode 230. The tines 620-670 and/or the ridges 610 and/or grooves may be used in various combinations along with other acute fixation techniques known in the art, such as, for example, a suture attachment point (not shown) on the lead 241.

Figure 7:
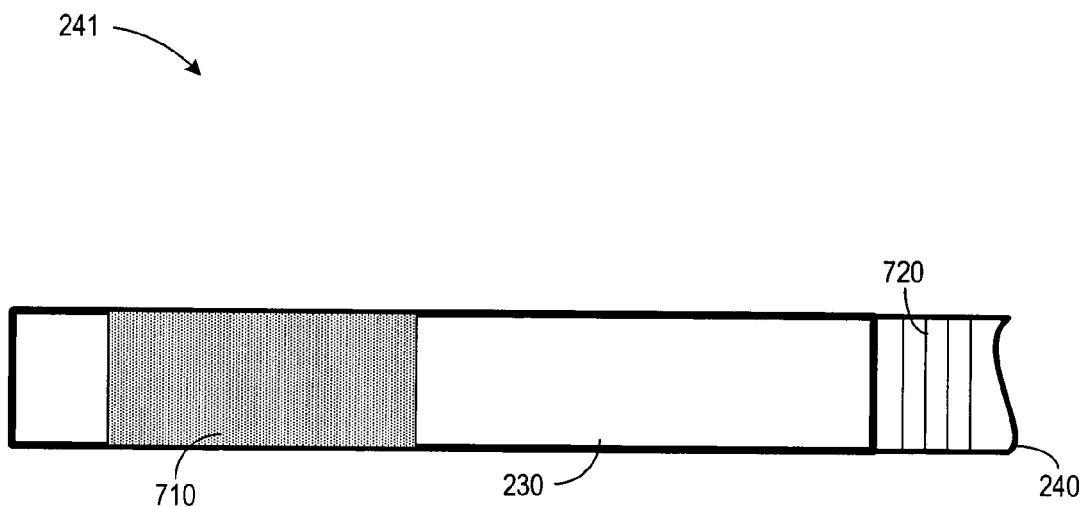
FIG. 7 is a magnified view of yet another embodiment of a lead having an electrode, the lead implemented to include fixation arrangements in accordance with the present invention.

Referring now to FIG. 7, another fixation arrangement in accordance with the present invention is illustrated. According to this embodiment, the fixation arrangement includes one or more textured surfaces or regions 710 on the lead body 240 and/or an electrode 230 of the lead 241. The textured surface(s) 710 may be employed as a sole chronic fixation method or in combination with other chronic fixation arrangements, such as a set of grooves 720 as is depicted in FIG. 7.

The textured surface 710 promotes tissue ingrowth to provide for chronic fixation of the lead body 240 into subcutaneous tissue. The textured surface 710 may be, for example, a porous region of the lead body 240, a coating having surface irregularities, dimples molded into the lead body 240 and/or a lead electrode 230, surface treatments from manufacturing processes such as sanding or scratching, or other suitable texturing.

Generally at least one acute fixation mechanism is employed in combination with chronic fixation mechanism, to allow sufficient time for the fixing of the chronic fixation mechanism into the subcutaneous tissue. An appropriate acute fixation mechanism is, for example, a suture placed at the distal end of the lead 241.

According to other fixation arrangements similar to those described above, and with reference to FIG. 7, the lead body 240 and/or the electrode 230 may be configured to incorporate tissue adhesion sites that facilitate chronic fixation of the lead body 240 and/or electrode 230 in subcutaneous tissue. For example, the adhesion sites may include voids in the sleeve of the lead body 240 at one or more locations of the sleeve. The adhesion sites may include exposed portions of one or more electrodes 230 or other exposed portions of the lead 241 insulation or covering.

According to another configuration, the adhesion sites may include a structure having a porous surface that promotes subcutaneous tissue in-growth or attachment at the adhesion sites. For example, a metallic annular structure may be disposed at the adhesion site. A metallic ring, for example, having porous surface characteristics may be employed to promote cellular adhesion at the adhesion site. The annular structure may incorporate the electrode 230 or be separate from the electrode 230.

In accordance with a further configuration, the adhesion sites may include a material that promotes subcutaneous tissue in-growth or attachment at the adhesion sites. For example, the bulk outer sleeve of the lead body 240 may be constructed that includes a first polymer material that substantially prevents tissue in-growth. Selective portions of the lead body 240 may include adhesion sites formed using a second polymer material that promotes tissue in-growth or attachment between the adhesion sites and subcutaneous tissue contacting the adhesion sites. The second polymer material may, for example, have a porosity, pore sizes or distribution of pore sizes that differ from that of the first polymer material. By way of further example, the second polymer material may differ in terms of hydrophobicity relative to the first polymer material.

In one particular configuration, the first polymer material may include a first type of PTFE (polytetrafluoroethylene), and the second polymer material of the adhesion sites may include a second type of PTFE. In one particular arrangement, the first type of PTFE includes a first type of ePTFE (expanded polytetrafluoroethylene), and the second type of PTFE includes a second type of ePTFE. The second type of ePTFE preferably differs from the first type of ePTFE in terms of one or more of porosity, pore sizes or distribution of pore sizes. Additional details of fixation approaches involving surface texturing, selective material use, and other arrangements that facilitate lead/electrode fixation via tissue ingrowth are disclosed in commonly owned U.S. patent application Ser. No. 10/004,708 (GUID.031US01) filed Dec. 4, 2001 and entitled "Apparatus and Method for Stabilizing an Implantable Lead," which is hereby incorporated herein by reference.

Figure 8A:
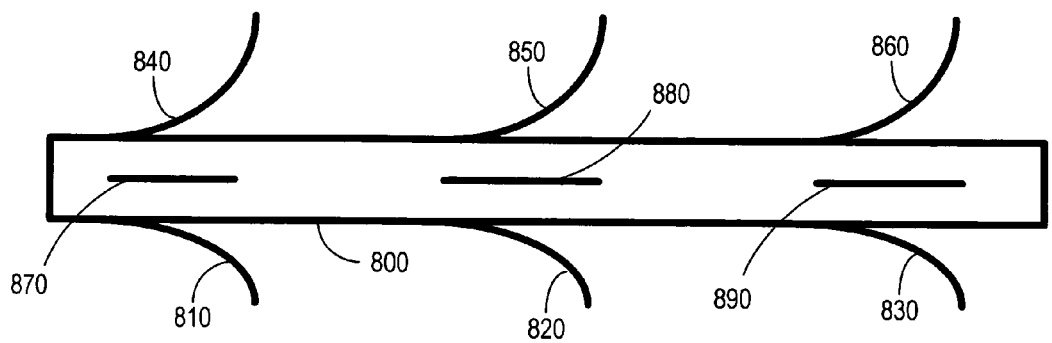
FIG. 8A is a magnified view of a further embodiment of a lead having an electrode, the lead implemented to include fixation arrangements in accordance with the present invention.
Figure 8B:
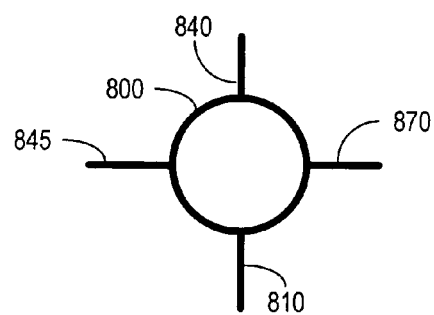
FIG. 8B is an end view of the embodiment illustrated in FIG. 8A.

Now referring to FIGS. 8A and 8B, details of acute fixation elements according to another embodiment of the present invention are shown. A lead 800 is illustrated that includes a plurality of tines 810, 820, 830, 840, 845 (FIG. 8B), 850, 860, 870, 880, and 890 (FIG. 8A). The tines 810-890 are shown disposed regularly with 90 degree circumferential placement, and regularly spaced along the length of the lead 800. However, other angles, regularity or irregularity, or number of tines may be employed in accordance with this embodiment. The tines 810-890 are shown, in this illustrative example, to be curved as they extend from the body of the lead 800. Curvature may assist in facilitating acute fixation by providing ease of movement of the lead 800 in a first direction (e.g., axial displacement in a distal direction), while helping to set the tines into tissue in response to movement in a second direction (e.g., axial displacement in a proximal direction). It is contemplated that the tines may be straight, or have a curvature tending away from or toward the body of the lead 800.

Figure 9A:
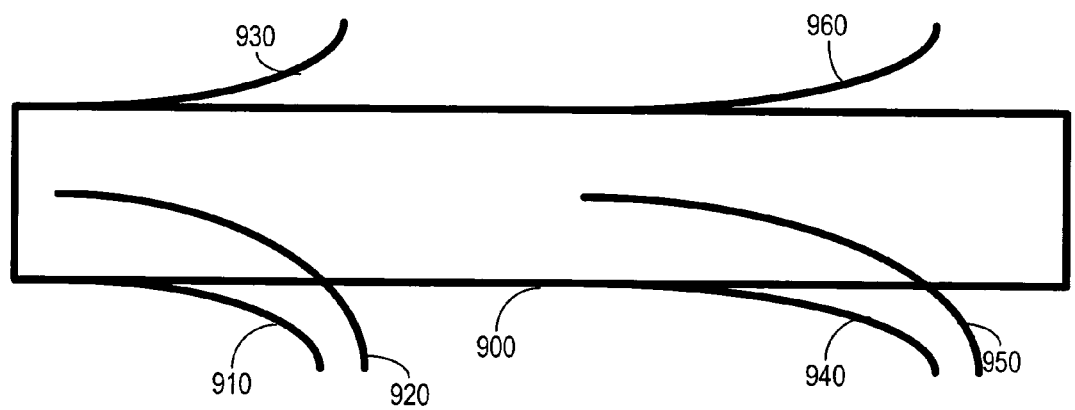
FIG. 9A is a magnified view of another embodiment of a lead having an electrode, the lead implemented to include a fixation arrangement in accordance with the present invention.
Figure 9B:
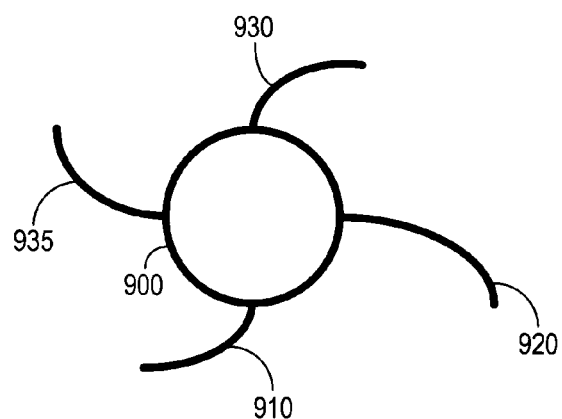
FIG. 9B is an end view of the embodiment illustrated in FIG. 9A.

Tines configured in accordance with the present invention may also be curved in more than one plane, as is illustrated in FIGS. 9A and 9B. A lead 900 (lead and/or electrode) is shown that includes tines 910, 920, 930, 935 (FIG. 9B), 940, 950, and 960 (FIG. 9A). As shown, the tines 910-960 are curved upward and away from the lead 900 relative to a longitudinal axis of the lead 900. The tines 910-960 are also curved around the circumference of the body of the lead 900 with respect to a second plane of reference.

The complex curvature illustrated in FIGS. 9A and 9B may be advantageous for optimally placing and fixing the lead 900 within subcutaneous tissue. This complex curvature provides for ease of inserting and withdrawing of the lead 900 when the lead 900 is rotated in a first direction. If the lead 900 is not rotated, the tines 910-960 set into the tissue. Further, if the lead 900 is rotated in the counter direction, the tines 910-960 may be forced into subcutaneous tissue.

Figure 9C:
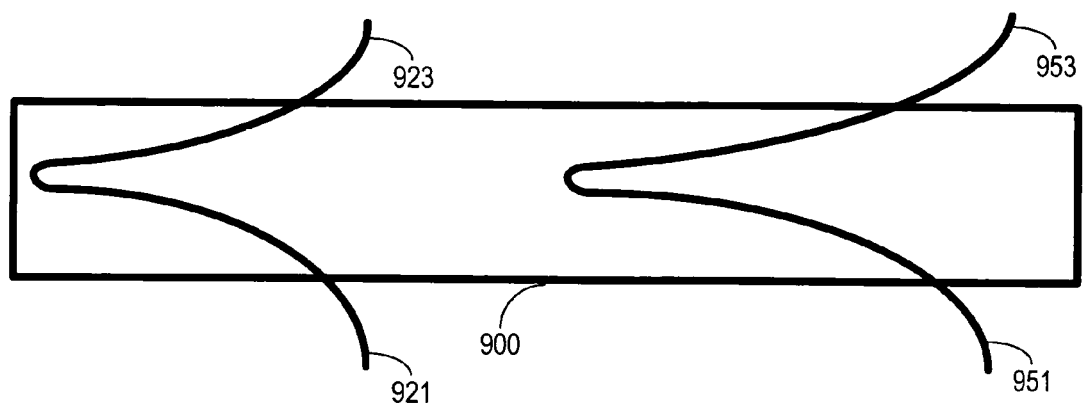
FIG. 9C is a magnified view of another embodiment of a lead having an electrode, the lead implemented to include a fixation arrangement in accordance with the present invention.
Figure 9D:
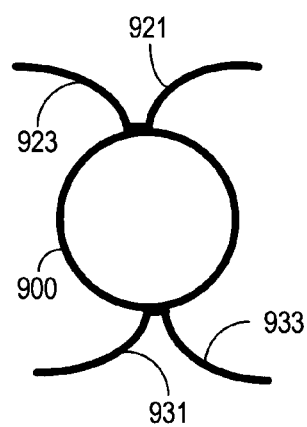
FIG. 9D is an end view of the embodiment illustrated in FIG. 9C.

Another tine configuration that employs complex curvature is illustrated in FIGS. 9C and 9D for optimally placing and fixing the lead 900 within subcutaneous tissue. This complex curvature provides for fixation from proximal displacement, and from rotation of the lead 900. Tines 921, 923, 931, 933, 951, and 953 set into the tissue due to their spring bias outwardly and upwardly from the lead 900. Placement of this type of lead fixation may be accomplished by direct distal insertion, to compress the tines 921, 923, 931, 933, 951, and 953 during placement and upon release of distal motion, the tines 921, 923, 931, 933, 951, and 953 spring outwardly from the lead 900 for fixation.

Figure 9E:
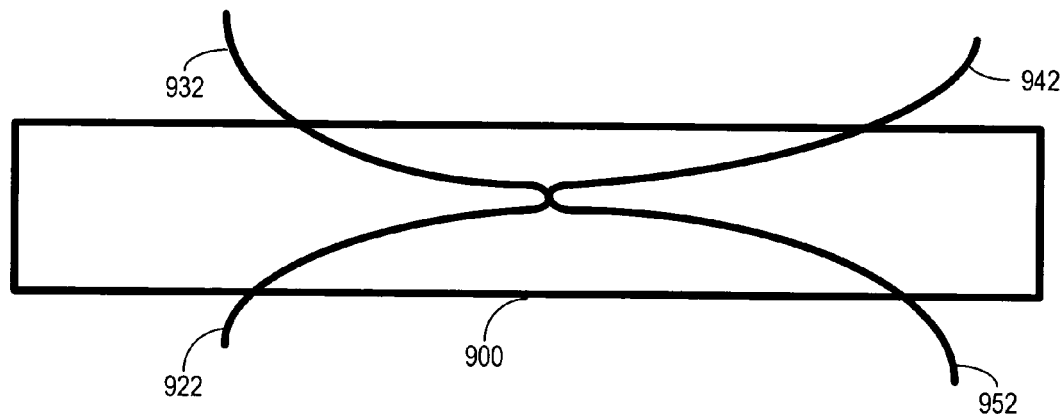
FIG. 9E is a magnified view of another embodiment of a lead having an electrode, the lead implemented to include a fixation arrangement in accordance with the present invention.
Figure 9F:
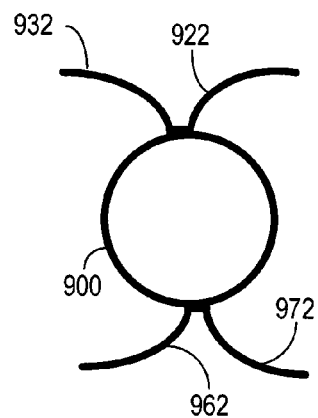
FIG. 9F is an end view of the embodiment illustrated in FIG. 9E.

A further tine configuration that employs complex curvature is illustrated in FIGS. 9E and 9F for optimally placing and fixing the lead 900 within subcutaneous tissue. This complex curvature provides for fixation from both proximal and distal displacement, and from rotation of the lead 900. Tines 922, 932, 942, 952, 962, and 972 set into the tissue due to their spring bias outwardly and upwardly from the lead 900. Placement of this type of lead fixation may be accomplished by utilization of a sheath, as described earlier, to compress the tines 922, 932, 942, 952, 962, and 972 during placement, and upon removal of the sheath, the tines 922, 932, 942, 952, 962, and 972 spring outwardly from the lead 900 for fixation.

Figure 9G:
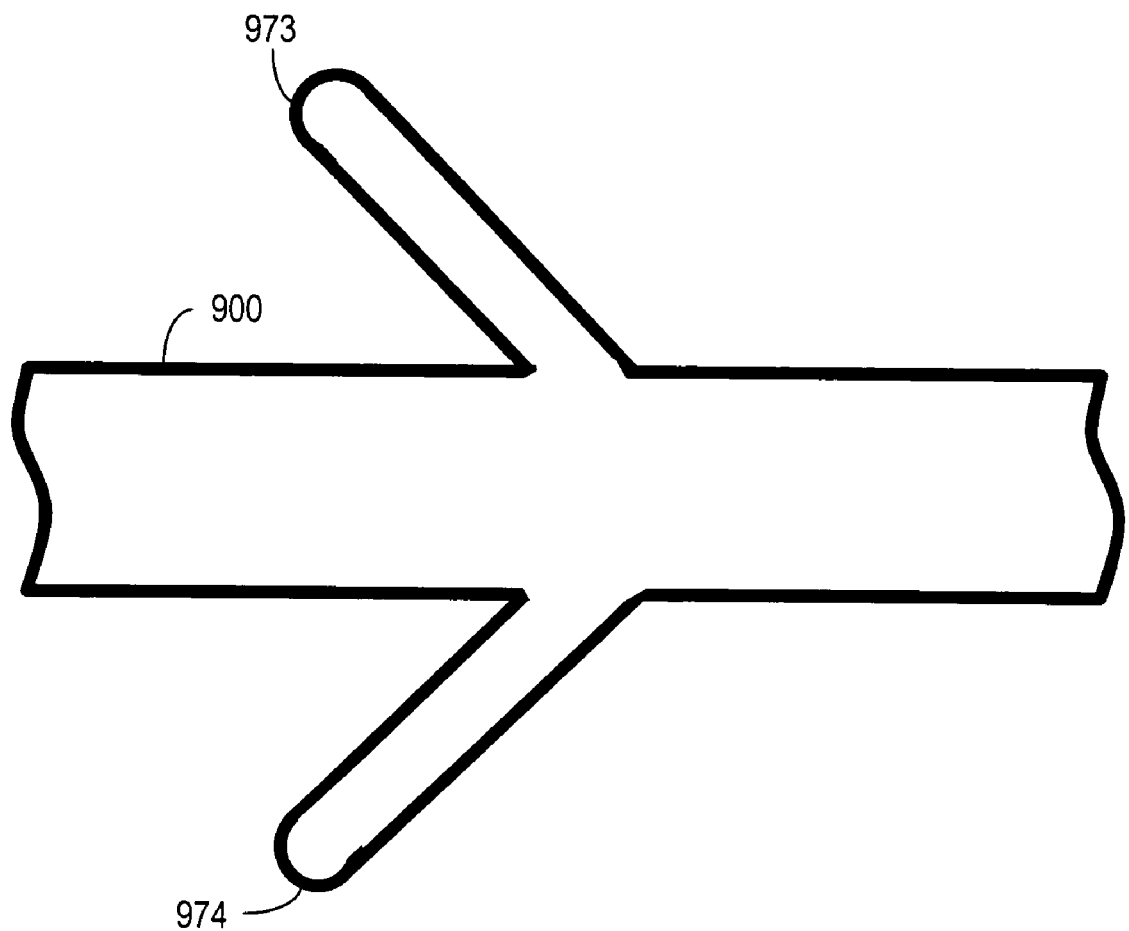
FIG. 9G is a magnified sectional view of another embodiment of a lead implemented to include a fixation arrangement in accordance with the present invention.

FIG. 9G is a magnified sectional view of another embodiment of a lead implemented to include a fixation arrangement in accordance with the present invention. Tines 973 and 974 set into the tissue due to their spring bias outwardly and upwardly from the lead 900. Placement of this type of lead fixation may be accomplished by utilization of a sheath, as described earlier, to compress the tines 973 and 974 during placement, and upon removal of the sheath, the tines 973 and 974 spring outwardly from the lead 900 for fixation.

Figure 10A:
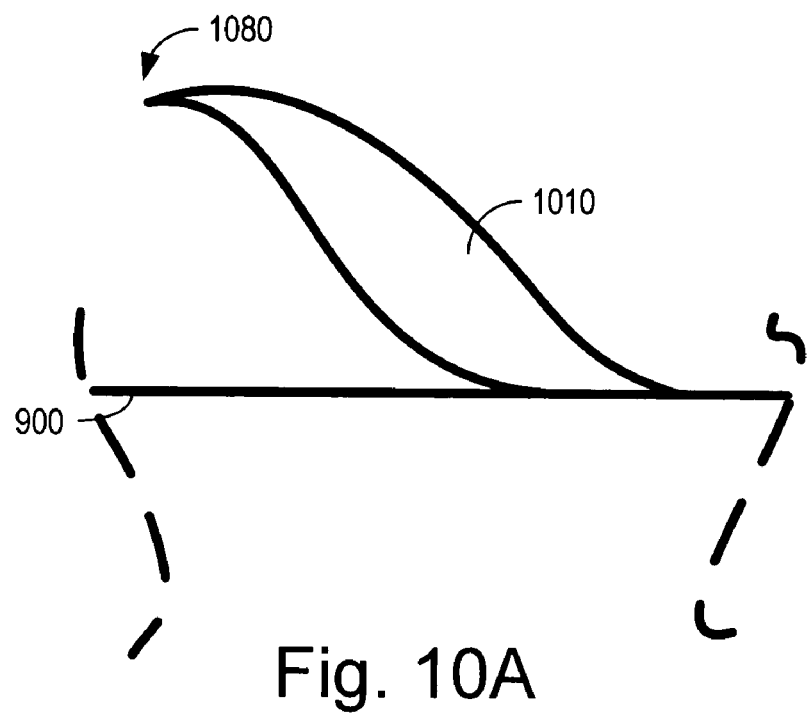
FIGS. 10A, 10B, 10C and 10D are sectional views of various tines in accordance with the present invention.

FIGS. 10A, 10B, 10C and 10D illustrate various shapes for tines in accordance with the present invention. In FIG. 10A, a tine 1010 is shown projecting from the lead 900. The tine 1010 has a single tip 1080. The tine 1010 is shaped to spring away from the lead 900 body.

For descriptive ease, consider a lead in the plane of FIGS. 10A, 10B, 10C and 10D, with the lead 900 moving from left to right in the plane of the figures. If the lead 900 were inserted, in this drawing from the left to the right, the tine 1010 would tend to collapse into the lead 900 and allow forward progress of the lead 900. If the lead 900 were to be pulled from right to left in FIG. 10A, the tine 1010 would tend to set into tissue by the single tip 1080.

Figure 10B:
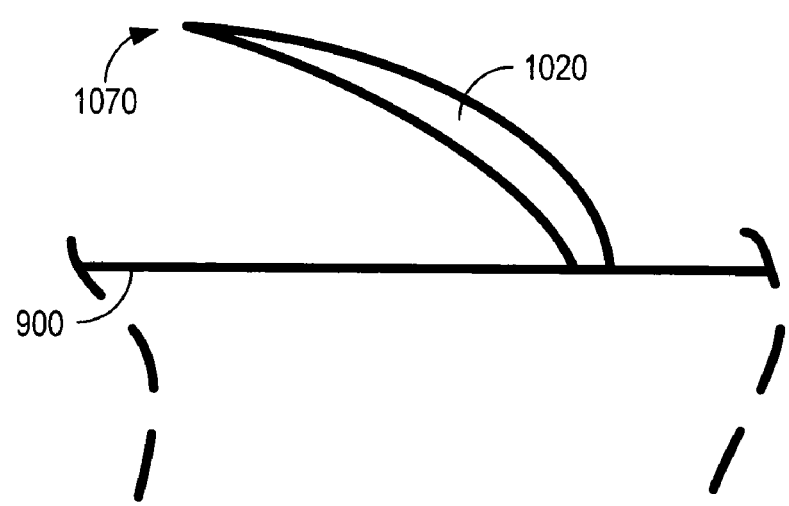

Similarly to the tine of FIG. 10A, a tine 1020 of FIG. 10B would also flex and set under the same movement. However, the tine 1020, not as substantial as the tine 1010 of FIG. 10A, would more easily collapse and compress under left to right motion, and may provide less resistance to right to left motion.

Figure 10C:
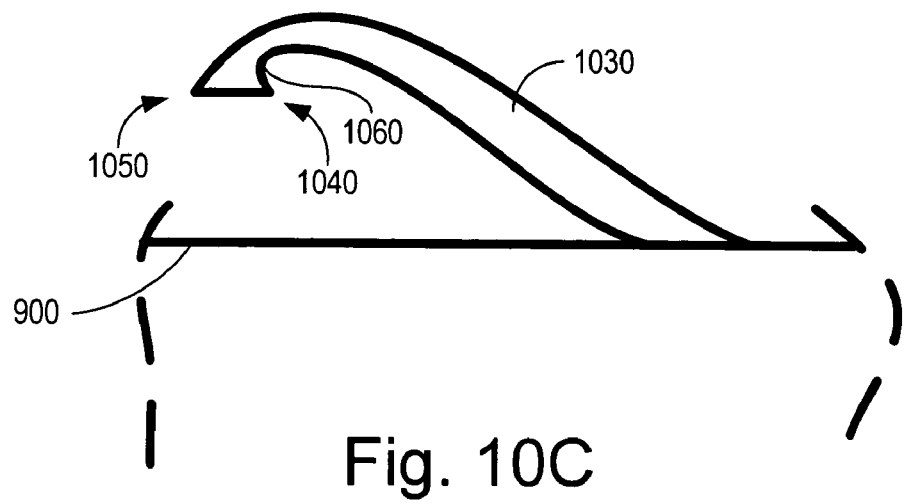

Referring now to FIG. 10C, a tine 1030 is illustrated with a first point 1050 and a second point 1040. The shape of the tine 1030, along with the second point 1040, creates a barb 1060. The barb 1060, similar to a fishhook barb, provides for not only resistance to right to left motion, but also for resistance to further left to right motion after being set. This arrangement provides for ease of insertion in a left to right direction, a resistance to right to left movement, and subsequently also provides resistance to further left to right movement after being set.

Figure 10D:
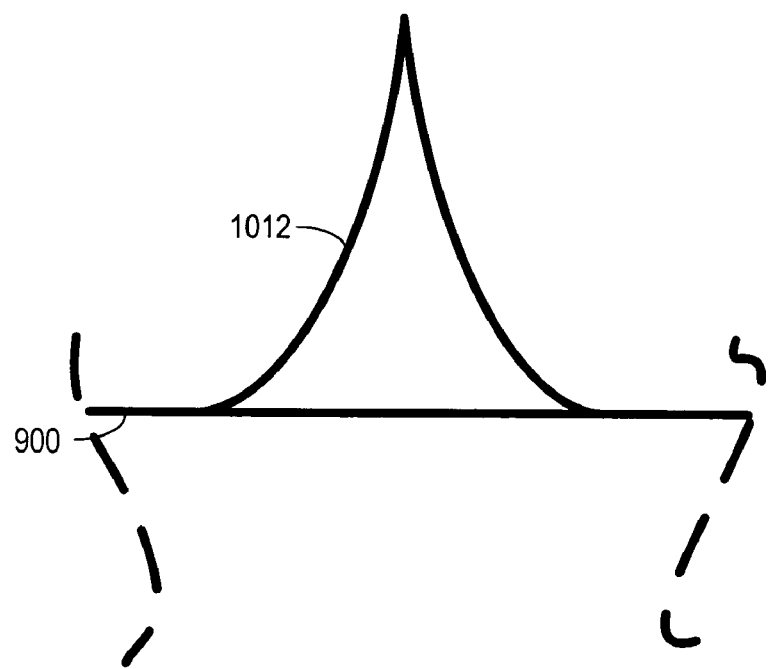

Referring to FIG. 10D, a straight tine 1012 is illustrated perpendicularly projecting from the lead 900 body. The straight tine 1012 may be compressed and/or spring biased in the lumen of a sheath (such as, for example, the sheath 320 in FIG. 3A) during delivery of the lead 900, such that the straight tine 1012 sets into tissue when the sheath is removed. In another embodiment, the rigidity of the straight tine 1012 may be designed such that a set level of resistance is provided by the straight tine 1012 when it is moved within tissue. By adjusting the rigidity, the level of fixation of the lead 900, and the associated ease of insertion/relocation, may be predetermined by design. Rigidity may be altered by material selection, geometry, of other means known in the art.

Figure 11:
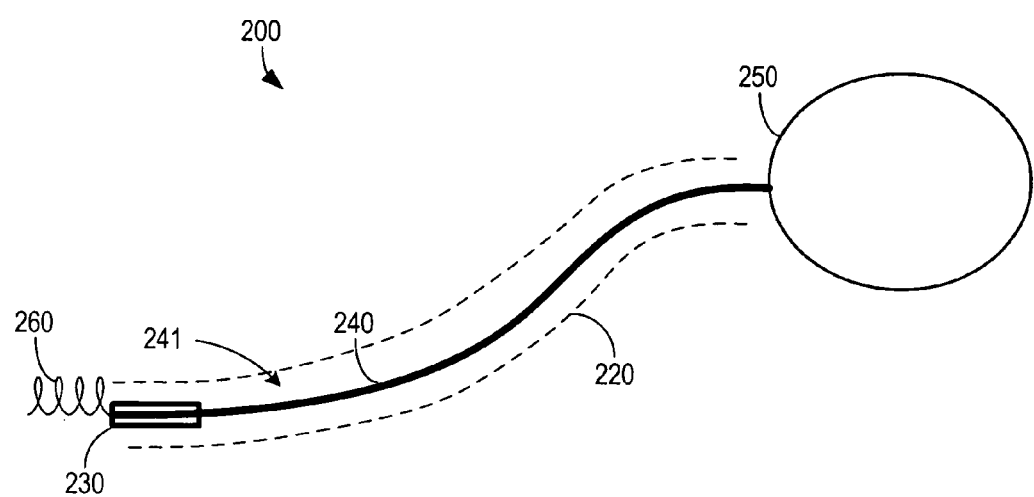
FIG. 11 illustrates a lead in accordance with the present invention, inserted in a dissected subcutaneous path leading from the can, where an offset helical electrode/fixation element is illustrated fixed to the tissue.

Referring now to FIG. 11, an ITCS system 200 is illustrated which includes a can 250 with a lead 241 inserted into a dissection path 220. The lead 241 includes an electrode 230, here illustrated at the distal end of the lead body 240. The subcutaneous dissection path 220 lies within subcutaneous tissue of a patient as illustrated in FIGS. 1A and 1B. An offset helix 260 is employed as a fixation element useable to fix the lead 241 into tissue in accordance with the present invention. Typically, the helix 260 is configured to define all or at least part of the electrode 230.

Figure 12:
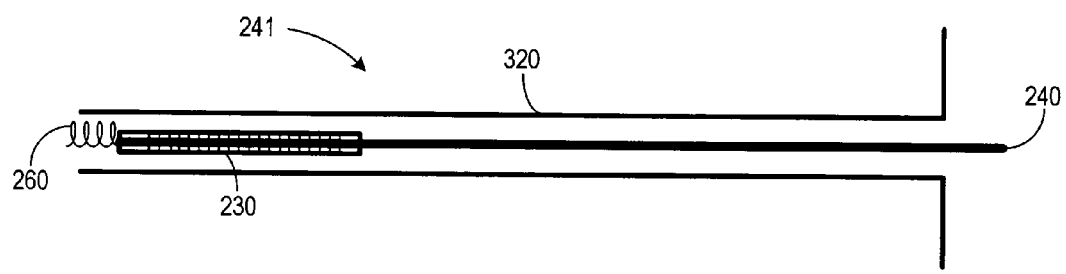
FIG. 12 is a plan view of a lead enclosed within a sheath prior to deployment of a fixation element in accordance with the present invention.

FIG. 12 illustrates the lead 241 inserted into the tear-away sheath 320 as described with an earlier embodiment. After placing the lead 241 in subcutaneous tissue, the sheath 320 is retracted from the subcutaneous tunnel, typically in a peel-away fashion. The lead 241 may be fixed into the tissue by rotating the lead 241 as will be described in further detail below.

Figure 13:
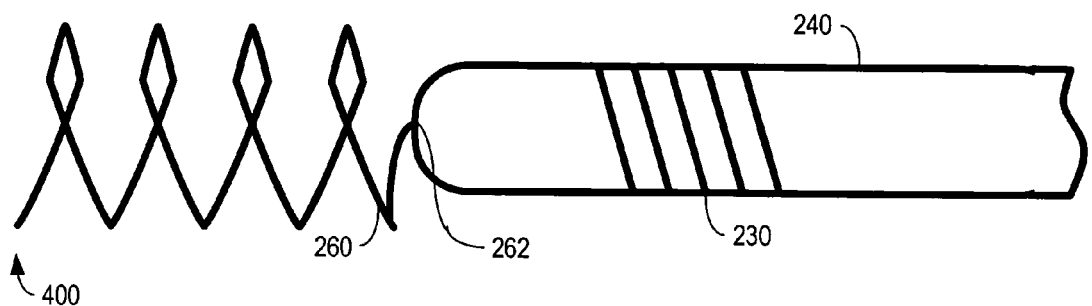
FIG. 13 is a magnified view of one embodiment of a lead having an electrode, the lead implemented to include a fixation arrangement in accordance with the present invention.
Figure 14:
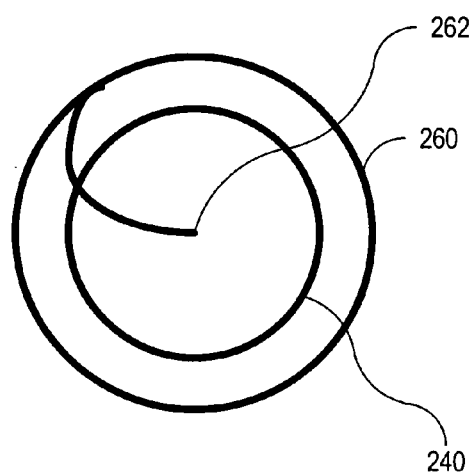
FIG. 14 is a magnified end view of the embodiment of FIG. 13.

FIGS. 13 and 14 show a plan view and end view respectively of an embodiment of the present invention. In FIG. 13, a helical coil 260 may be used as a fixation element to fix the lead body 240 into tissue when the electrode 230 is positioned in a desired location. The helical coil 260 is attached to the distal end of the lead body 240 at attachment point 262. Rotation of the lead body 240 causes rotation of the helical coil 260, thereby rotating sharp end 400.

Although helical coil 260 is illustrated having uniform pitch, cylindrical cross-section constant thickness of coil, it is contemplated that any helical or screw-like structure may be used in accordance with the present invention. The helix may be of non-uniform and/or tapering cross-section; the pitch may be non-uniform; and the shape and thickness of the coil may be varied without departing from the scope of the present invention.

As the lead 241 is rotated, the sharp end 400 contacts the wall of the dissected tissue path and penetrates into subcutaneous tissue. As the lead 241 is further rotated, the sharp end 400 burrows through the tissue, repeatedly penetrating the wall and progressing forward as the winding of the helical coil 260 dictates. This effectively screws the helical coil 260 into the wall of the tissue, thus fixing the lead 241.

In another embodiment, the helical coil 260 may be rotatable independently of the lead 241. As the helical coil 260 is rotated or formed via extension, the sharp end 400 contacts the wall of the dissected tissue path and penetrates into subcutaneous tissue. As the helical coil is further rotated or further extended, the sharp end 400 burrows through the tissue, repeatedly penetrating the wall and progressing forward as the winding of the helical coil 260 dictates. This effectively screws the helical coil 260 into the wall of the tissue, thus fixing the lead 241.

In the embodiment illustrated in FIGS. 13 and 14, the helical coil 260 is seen to be larger in diameter than the lead body 240. An advantage of employing the helical coil 260 that is larger than the lead body 240 is the assurance that as the lead lies within the dissected tissue tunnel, the sharp end 400 penetrates the tunnel wall and provide fixation when rotated. If the helical coil 260 were the same size or smaller than the lead body 240 diameter, the lead body may prevent the sharp end 400 from initiating penetration unless the lead body 240 is pushed distally along the dissection tunnel until penetration occurs. This pushing of the lead may cause the electrode 230 to be moved distally from an optimum fixation location.

Figure 15:
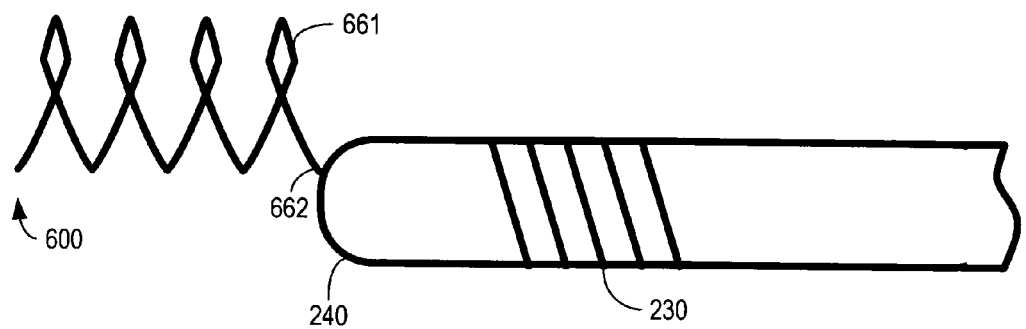
FIG. 15 is a magnified view of a further embodiment of a lead having an electrode, the lead implemented to include a fixation arrangement in accordance with the present invention.
Figure 16:
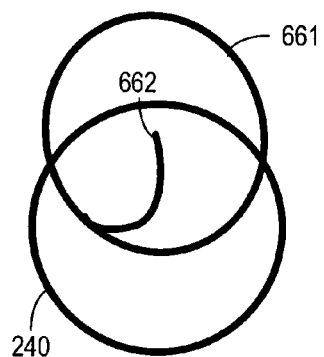
FIG. 16 is a magnified end view of the embodiment of FIG. 15.

Referring now to FIGS. 15 and 16, a plan view and end view respectively of another embodiment of the present invention is illustrated. In FIG. 15, an offset helical coil 661 may be used as a fixation element to fix the lead body 240 into tissue when the electrode 230 is positioned in a desired location. The offset helical coil 661 is attached to the distal end of the lead body 240 at attachment point 662. Rotation of the lead body 240 causes rotation of the offset helical coil 661, rotating sharp end 600.

As the lead body 240 is rotated, the sharp end 600 contacts the wall of the dissected tissue path and penetrates into subcutaneous tissue. As the lead body 240 is further rotated, the sharp end 600 burrows through the tissue, repeatedly penetrating the wall and progressing forward as the winding of the offset helical coil 661 dictates. This effectively screws the offset helical coil 661 into the wall of the tissue, thus fixing the lead 241.

In the embodiment illustrated in FIGS. 15 and 16, as best seen in FIG. 16, the offset helical coil 661 is seen to have an offset central axis relative to the longitudinal axis of the lead body 240. An advantage of employing the offset helical coil 661 offset from the lead body 240 is the assurance that as the lead lies within the dissected tissue tunnel, the sharp end 600 penetrates the tunnel wall and provides fixation when rotated.

Coils 260 and 661 may be manufactured using a spring material such as, for example, metal, such that coils 260 and 661 deform within the sheath 320 when being advanced to their fixation locations. Upon removal of the sheath 320, coils 260 and 661 spring into their larger or offset configurations to affect fixation into tissue. Coils 260 and 661 may also be manufactured using a shape memory alloy such as, for example, Nitinol, such that coils 260 and 661 have a first, non-penetrating shape, when being advanced through the dissection path. Upon being subjected to body temperature or artificially heated, coils 260 and 661 return to a shape such as described above to affect fixation.

It should be understood that any number, type, or combination of fixation elements have been contemplated, and that the number, types, and combinations presented above are by way of example only. Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable lead, comprising:
 a lead body comprising a sheath, the sheath having a proximal end, a distal end, and a distal tip terminating the distal end, the distal tip having a body cross-sectional diameter;
 a delivery sheath having a lumen, a distal end, and a distal tip terminating the distal end, the lead body configured to translate longitudinally within the lumen;
 a cardiac electrode supported by the lead body, the cardiac electrode configured for subcutaneous non-intrathoracic placement within a patient; and
 a fixation element provided on the distal tip of the sheath of the lead body, the fixation element comprising a helical coil configured to be deployed distal of the distal tip of the sheath of the lead body, the helical coil including a tissue penetrating tip, a portion of the helical coil configured to extend radially beyond the body cross-sectional diameter of the distal tip of the sheath of the lead body and actively secure the lead in subcutaneous non-intrathoracic tissue in a deployed configuration, the helical coil compressed by, and substantially contained within, the lumen of the delivery sheath in a non-deployed configuration, the implantable lead configured such that retraction of the distal tip of the delivery sheath past the distal tip of the sheath of the lead body to a location proximal of the distal tip of the sheath of the lead body transitions the helical coil from the non-deployed configuration to the deployed configuration.

2. The lead according to claim 1, wherein the fixation element has a fixation element cross-sectional diameter, and wherein the fixation element cross-sectional diameter is larger than the body cross-sectional diameter of the distal tip of the sheath of the lead body.

3. The lead according to claim 1, wherein the helical coil is coupled to the lead body to facilitate independent rotation of the helical coil relative to the lead body.

4. The lead according to claim 1, wherein a cross-sectional diameter of the helical coil is substantially equal to the body cross-sectional diameter of the distal tip of the sheath while in the non-deployed configuration.

5. The lead according to claim 1, wherein the distal tip of the sheath of the lead body has a longitudinal axis and the fixation element has a fixation element longitudinal axis, and wherein the longitudinal axis of the distal tip of the sheath is non-coincident with respect to the fixation element longitudinal axis in the deployed configuration.

6. The lead according to claim 1, wherein the helical coil is formed from a shape memory alloy.

7. The lead according to claim 1, wherein the fixation element is formed from a material having a spring memory.

8. The lead according to claim 1, wherein the fixation element is electrically insulated from the electrode.

9. The lead according to claim 1, wherein the fixation element is part of the electrode.

10. The lead according to claim 1, wherein:
the distal tip of the sheath of the lead body comprises a longitudinal axis; and
the fixation element comprises a longitudinal axis aligned in a non-coaxial parallel relationship with respect to the longitudinal axis of the distal tip of the sheath of the lead body in the deployed configuration.

11. The lead according to claim 1, wherein the helical coil has a non-uniform cross-sectional diameter along the helical coil.

12. An implantable lead system, comprising:
a lead body comprising a sheath, the sheath having a proximal end, a distal end, and a distal tip terminating the distal end, the distal tip of the sheath having a body cross-sectional diameter and a longitudinal axis;
a cardiac electrode supported by the lead body, the cardiac electrode configured for subcutaneous non-intrathoracic placement within a patient;
a fixation element provided on the distal tip of the sheath and extending distal of the distal tip of the sheath, the fixation element comprising a longitudinal axis non-coincident with the longitudinal axis of the distal tip of the sheath, and a helical coil including a tissue penetrating tip and configured to actively secure the lead body or electrode in subcutaneous non-intrathoracic tissue, a portion of the helical coil configured to radially extend beyond the body cross-sectional diameter of the distal tip of the sheath.

13. The lead system according to claim 12, further comprising a delivery apparatus comprising a delivery sheath, the delivery sheath having a proximal end of the delivery sheath, a distal end of the delivery sheath, a distal tip of the delivery sheath terminating the distal end of the delivery sheath, and a lumen extending between the proximal end of the delivery sheath and the distal tip of the delivery sheath, the delivery sheath configured to:
contain the lead body within the lumen of the delivery sheath, the helical coil compressed by the lumen of the delivery sheath;
introduce the lead to a desired subcutaneous non-intrathoracic location within the patient; and
separate from the lead body and leave the lead body in the desired subcutaneous non-intrathoracic location, wherein the implantable lead system is configured such that the helical coil radially springs beyond the body cross-sectional diameter of the distal tip of the sheath of the lead body upon retraction of the distal tip of the delivery sheath past the fixation element to a location proximal of the distal tip of the sheath of the lead body.

14. The lead system according to claim 12, wherein the helical coil is coupled to the lead body to facilitate independent rotation of the helical coil relative to the lead body.

15. The lead according to claim 12, wherein
the fixation element comprises a longitudinal axis aligned in a non-coaxial parallel relationship with respect to the longitudinal axis of the distal tip of the sheath of the lead body.

16. The lead system according to claim 12, wherein the fixation element has a fixation element cross-sectional diameter, and wherein the fixation element cross-sectional diameter is larger than the body cross-sectional diameter of the distal tip of the sheath of the lead body.

17. The lead system according to claim 12, wherein the helical coil is formed from a shape memory alloy.

18. The lead system according to claim 12, wherein the fixation element is formed from a material having a spring memory.

19. The lead system according to claim 12, wherein the fixation element is electrically insulated from the electrode.

20. The lead system according to claim 12, wherein the fixation element is part of the electrode.

21. The lead system according to claim 12, wherein the lumen of the delivery sheath is dimensioned to compress the fixation element while permitting axial displacement of the lead within the lumen.

22. An implantable lead, comprising:
a lead body comprising a sheath, the sheath having a proximal end, a distal end, and a distal tip terminating the distal end of the sheath and the lead body, the distal tip having a body cross-sectional diameter;
a delivery sheath having a lumen, a proximal end of the delivery sheath, a distal end of the delivery sheath, and a distal tip terminating the distal end of the delivery sheath, the lead body translatable within the lumen of the delivery sheath;
a cardiac electrode supported by the lead body, the cardiac electrode configured for subcutaneous non-intrathoracic placement in a patient; and
means for actively fixing the lead body within subcutaneous non-intrathoracic tissue, the active fixing means comprising helical fixing means disposed on the distal tip of the sheath of the lead body and extending distal of the distal tip of the sheath of the lead body, the helical fixing means configured to penetrate subcutaneous tissue and radially extend beyond the body cross-sectional diameter of the distal tip of the sheath of the lead body in a deployed configuration upon retraction of the distal tip of the delivery sheath to a location proximal of the distal tip of the sheath of the lead body, the helical coil compressed by, and contained within, the lumen of the delivery sheath in a non-deployed configuration.

23. The lead according to claim 22, wherein the active fixing means comprises means for rotatably fixing one or both of the lead body and the cardiac electrode within the subcutaneous non-intrathoracic tissue.

24. The lead according to claim 22, further comprising means for modifying a position or an orientation of the fixing means.

25. The lead according to claim 22, wherein the lumen of the delivery means is dimensioned to at least partially collapse the fixing means while permitting axial displacement of the lead body within the lumen.

* * * * *